United States Patent

Gabetta et al.

Patent Number: 5,407,674
Date of Patent: Apr. 18, 1995

[54] TAXANE HAVING ANTITUMOR ACTIVITY

[75] Inventors: Bruno Gabetta; Ezio Bombardelli, both of Milan, Italy

[73] Assignee: Indena S.p.A., Milan, Italy

[21] Appl. No.: 88,319

[22] Filed: Jul. 7, 1993

[30] Foreign Application Priority Data

May 21, 1993 [IT] Italy .............................. RM93A0334

[51] Int. Cl.$^6$ .................. A61K 35/78; A61K 31/335; C07C 69/76
[52] U.S. Cl. ................................ 424/195.1; 514/449; 514/783; 560/104
[58] Field of Search ................ 560/104; 514/449, 783; 424/195.1

[56] References Cited

U.S. PATENT DOCUMENTS

| | | | |
|---|---|---|---|
| 4,206,221 | 6/1980 | Miller et al. | 514/449 |
| 4,942,184 | 7/1990 | Haugwitz et al. | 514/449 |
| 5,157,049 | 10/1992 | Haugwitz et al. | 514/449 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,250,683 | 10/1993 | Holton et al. | 544/60 |
| 5,250,722 | 10/1993 | Bombardelli et al. | 560/104 |

Primary Examiner—Douglas W. Robinson
Assistant Examiner—Howard C. Lee
Attorney, Agent, or Firm—Mathews, Woodbridge & Collins

[57] ABSTRACT

The present invention relates to a new taxane having the structure (1), which is isolatable from root bark of plants of the Taxus genus. The compound (1) is endowed with antitumor activity higher than the one of taxol, the former being active, unlike the latter, also against adriamicine resistant cells and as antileukemic drug.

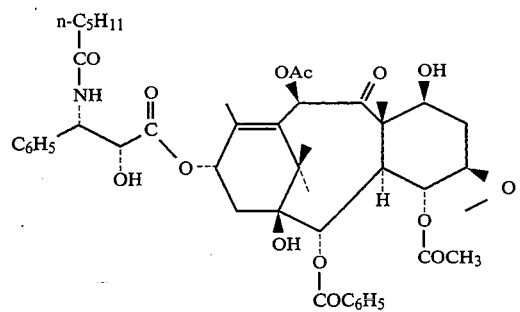

8 Claims, No Drawings

TAXANE HAVING ANTITUMOR ACTIVITY

The present invention relates to a new diterpene with taxane nucleus having antitumor activity. From spectrometric analysis, the new compound was given the structural formula (1), corresponding to the ester at the 13-position of 5β,20-epoxy-1,2α,4,7β,10β,13α-hexahydroxytax-11-en-9-one 4,10-diacetate 2-benzoate with (2R, 3S)-N-hexanoyl-3-phenylisoserine.

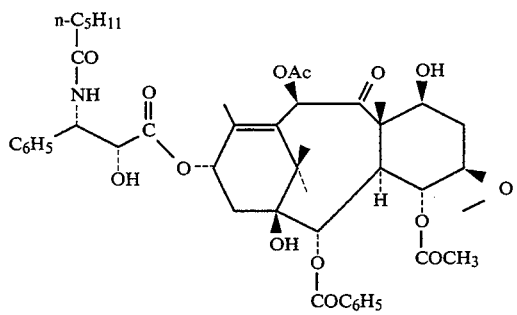

The compound of formula (1) has been isolated from the root bark of the Taxus genus, with yields ranging from 0.02 to 0.06%.

The vegetal material, which the compound (1) is extracted from, preferably consists of the roots of yew cultivar, for example the bark of *Taxus media* cv *Hicksii*. This cultivar is currently used with ornamental purposes for garden dressing. This fact allows to avoid the indiscriminate harvesting of the roots of spontaneous yew trees, whose growth is notoriously slow, and their consequent rapid extinction.

The compound (1) is extracted by means of chlorinated solvents, for example dichloromethane, pure or in admixture with alcohols, for example methyl and ethyl alcohol. The extraction of the vegetal material can be carried out also by using ketones, for example acetone, pure or in admixture with water.

The root bark extract contains, in addition to compound (1), a series of other well-known taxans, such as taxol (2), cephalomanine (3), and their respective 10-deacetyl derivatives (4) and (5). The separation of (1) from the above taxanes requires a purification through column chromatography.

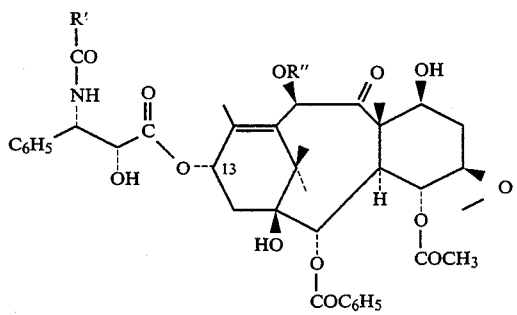

2 R' = C₆H₅; R" = COCH₃

3 R' = —C(CH₃)=CHCH₃; R" = H

4 R' = C₆H₅; R" = H

5 R' = —C(CH₃)=CHCH₃; R" = H

For this purpose silica gel is preferably used as the stationary phase. Solvent mixtures, consisting of an aliphatic hydrocarbon, for example n-hexane, cyclohexane or n-heptane, or aromatic hydrocarbon, for example toluene, together with a higher polarity solvent, such as ethyl acetate or acetone are used as eluents.

The compound (1), once recovered from the chromatographic fractions containing it, is isolated after crystallization from whether acetone or diisopropyl ether or mixtures thereof with n-hexane or n-heptane.

The new compound (1) shows remarkable structural affinities with the antitumor drug taxol (2), from which it differs for the kind of side chain bonded at the 13-position of the taxane nucleus. Therefore, the compound (1) can be available, besides extraction from vegetal material, by semisynthesis through processes similar to the ones used for the production of taxol (2) (I. Ojima et al, Tetrahedron 48, 6985, 1992).

Due to the structural affinities between the compound (1) and taxol (2), a similar antitumor activity from the former could be expected.

Indeed, in vitro activity of (1) against several tumoral lines, for example the one relating to breast, lung, colon and ovary cancer, is comparable with the taxol's one, as reported in Table 1. However, the new taxane (1) surprisingly shows a higher activity than the taxol's one with respect to adriamicine (ADR) resistant tumor cells and to leukemic cells. Table 1-Comparison between taxane (1) and taxol (2) antiblastic activity on various tumoral lines (IC50, nM).

| Tumor cells | Taxane (1) | Taxol (2) |
|---|---|---|
| L1210 (murine leukemia) | 3.6 ± 0.3 | 57.0 ± 3.0 |
| A121 (human ovarian) | 8.6 ± 0.4 | 6.3 ± 0.3 |
| A549 (human NSCLC) | 3.9 ± 0.3 | 5.4 ± 0.5 |
| HT-29 (human colon) | 5.4 ± 0.5 | 6.0 ± 0.6 |
| MCF7 (human breast) | 2.2 ± 0.1 | 4.3 ± 0.5 |
| MCF7-ADR (ADR resistant) | 430 ± 22 | >1000 |

In in vivo studies, the compound (1), administered in aqueous solution containing Cremophor(R), proved to be effective against tumors implanted into nude mice. Accordingly, the taxan (1) is expected to be used as antitumor drug for the treatment of liquid tumors and drug-resistant tumors, such as adriamicine-resistant tumors.

According to the active doses found in the animal, the dose of the compound (1) in man should be comprised between 150 and 250 mg/m² with cycles repeated at a two or three-week interval until the metastasis disappearance.

The following example illustrates the preparation of the compound of the present invention.

EXAMPLE 1

Ester at 13-position of 5β,20-epoxy-1,2α,4,7β,10β,13α-hexahydroxytax-11-en-9-one 4,10-diacetate 2-benzoate with (2R,3S)-N-hexanoyl-3-phenylisoserine (formula 1)

50 kg of *Taxus media* cv *Hicksii* powdered bark were extracted at room temperature with 130 liters and subsequently three times with 80 liters of a 9:1 methylene chloride/methanol mixture, each extraction running 24 hours.

The gathered extracts were vacuum concentrated and the residue (4300 g) was taken up with 23 liters of a 9:1 toluene acetone mixture. After having filtered the insoluble matter, the solution was purified by column chromatography through 27 kg of silica gel, eluting with the same solvent mixture. The fractions containing the product (1) were gathered and evaporated to dryness under vacuum. The residue was crystallized from 80 ml of a 1:1 n-hexane/acetone mixture, 17,5 g of (1), m.p. 209°, [α]$_D$—42°(c=0.3, MeOH), M+a m/z 847, were obtained.

The spectrophotometric data of the compound (1) are the following:

IR (nujol): 3500–3300, 1710, 1640 cm$^{-1}$

UV (MeOH): 222 (13900), 232 (16250), 274 (1130), 282 (990) nm

CIMS (NH$_3$), m/z 865 (40%, M+NH$_4$), 848 (10, MH), 586 (30, M+NH$_4$ —279)

$^1$H-NMR (300 MHz, CDCl$_3$, ppm, J in Hz) 5,66 (d, J=7,0; H-2), 3,78 (d, J=7,0; H-3), 4,93 (dd, J$_1$=9,4, J$_2$=2,0; H-5), 2,54 (ddd, J$_1$=15,5, J$_2$=9,4, J$_3$=6,6; H-6α), 1,84 (ddd, J$_1$=15,5, J$_2$=10,9; J$_3$=2,0; H-6β), 4,39 (ddd, J$_1$=10,9, J$_2$=6,6, J$_3$=4,1; H-7), 6,28 (s, H-10), 6,23 (t, J=6,23; H-13), 2,24–2,32 (2H, m; H-14), 1,26 (s, H-16), 1,14 (s, H-17), 1,81 (d, J=1,2; H-18), 1,67 (s, H-19), 4,17 (d, J=8,6; H-20α), 4,28 (d, J=8,6; H-20β), 4,65 (dd, J$_1$=4,9, J$_2$=2,5; H-2'), 5,56 (dd, J$_1$=8,9, J$_2$=2,5; H-3'), 2,18 (t, J=7,3; H-2''), 1,56 (m; H-3''), 1,28–1,20 (m; H-4'' e H-5''), 0,83 (t, J=6,7; H-6''), 8,10 (d, J=7,8; PhCO H-2 e 6), 7,50 (t, J=7,8; PhCO H-3 e 5), 7,61 (t, J=7,8; PhCO H-4), 7,38 (m; 3'-Ph H-2,3,4,5,6), 2,34 (s, COCH$_3$), 2,24 (s, COCH$_3$), 6,25 (d, J=8,9; NH), 2,49 (d, J=4,1; 7-OH), 1,84 (s, 1-OH), 3,55 (d, J=4,9; 2'-OH).

$^{13}$C-NMR (75,43 Hz, CDCl$_3$): 78,99 (C-1), 74,93 (C-2), 45,57 (C-3), 81,07 (C-4), 84,37 (C-5), 35,59 (C-6), 72,15 (C-7), 58,56 (C-8), 203,63 (C-9), 75,55 (C-10), 138,06 (C-11), 142,05 (C-12), 72,29 (C-13), 35,59 (C-14), 43,18 (C-15), 26,79 (C-16), 21,86 (C-17), 14,81 (C-18), 9,54 (C-19), 76,46 (C-20), 172,78 (C-1'), 73,16 (C-2'), 54,53 (C-3'), 172,90 (C-1''), 36,55 (C-2''), 25,34 (C-3''), 31,29 (C-4''), 22,28 (C-5''), 13,83 (C-6''), 129,09 (PhCO C-1), 130,19 (PhCO C-2 e C-6), 128,68 (PhCO C-3 e C-5), 133,68 (PhCO C-4), 133,11 (Ph C-1), 126,94 (Ph C-2 e C-6), 128,93 (Ph C-3 e C-5), 128,23 (Ph C-4), 22,58 (COCH$_3$), 20,84 (COCH$_3$), 171,23 (COCH$_3$), 170,23 (COCH$_3$), 166,95 (PhCO). C$_{46}$H$_{57}$NO$_{14}$: found % C=65,11; H=6,86; N=1,60 calc. % C=65,15; H=6,78; N=1,65.

We claim:

1. A substantially pure compound which is the 13α-(2R,3S)-N-hexanoyl-3-phenyl serine ester of 5β,20-epoxy-1,2α,4,7β,10β,13α-hexahydroxytax-11-en-9-one, said ester having the formula:

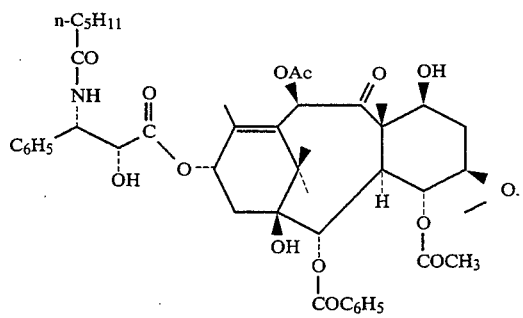

2. A process for the preparation of a compound according to claim 1 which comprises:
   (i) extracting the vegetal material of yew cultivar with at least one chlorinated hydrocarbon or mixtures of at least one chlorinated hydrocarbon and at least one lower alkanol;
   (ii) removing the solvent from the extracts obtained in step (i);
   (iii) chromatographing the residue obtained in step (ii) with an eluent comprising a mixture of (a) at least one aliphatic hydrocarbon or aromatic hydrocarbon and (b) at least one solvent having a higher polarity than said hydrocarbon; and
   (iv) recrystallizing at least one chromatographic fraction containing said compound obtained in step (iii).

3. The process according to claim 2 wherein said vegetal material is *Taxus media* cv *Hicksii* root bark.

4. The process according to claim 2 wherein said chlorinated hydrocarbon is methylene chloride and said lower alkanol is methanol.

5. The process according to claim 2 wherein the residue obtained in step (ii) is chromatographed on silica gel as a stationary phase and said eluent comprises toluene as said aromatic hydrocarbon and acetone as said solvent having a higher polarity.

6. The process according to claim 2 wherein the recrystallization solvent comprises at least one of acetone and diisopropyl ether.

7. The process according to claim 6 wherein the recrystallization solvent comprises at least one of acetone and diisopropyl ether in admixture with at least one of n-hexane and n-heptane.

8. A process for the preparation of a compound according to claim 1 which comprises:
   (i) extracting *Taxus media* cv *Hicksii* root bark with methylene chloride or mixtures of methylene chloride and methanol;
   (ii) removing the solvent from the extracts obtained in step (i);
   (iii) chromatographing the residue obtained in step (ii) on silica gel as a stationary phase with an eluent comprising toluene and acetone; and
   (iv) recrystallizing at least one chromatographic fraction containing said compound obtained in step (iii) with a recrystallization solvent comprises acetone, diisopropyl ether, or mixtures of acetone or diisopropyl ether with n-hexane or n-heptane.

* * * * *